US010478267B2

(12) United States Patent
Guenst et al.

(10) Patent No.: US 10,478,267 B2
(45) Date of Patent: Nov. 19, 2019

(54) ORAL IRRIGATOR

(71) Applicant: ToothShower LLC, Collegeville, PA (US)

(72) Inventors: Lisa Michelle Guenst, Collegeville, PA (US); Robert James Andrake, Abington, PA (US); Brian Michael Orme, Phoenixville, PA (US); Jeremy Mark Fallis, Jr., Bethlehem, PA (US); Daniel Shanahan, Philadelphia, PA (US)

(73) Assignee: TOOTHSHOWER LLC, Collegeville, PA (US)

( * ) Notice: Subject to any disclaimer, the term of this patent is extended or adjusted under 35 U.S.C. 154(b) by 489 days.

(21) Appl. No.: 15/401,144

(22) Filed: Jan. 9, 2017

(65) Prior Publication Data

US 2018/0193108 A1    Jul. 12, 2018

(51) Int. Cl.
*A61C 1/00* (2006.01)
*A61C 17/02* (2006.01)
(Continued)

(52) U.S. Cl.
CPC ........ *A61C 1/0092* (2013.01); *A61C 17/0202* (2013.01); *A61C 17/028* (2013.01);
(Continued)

(58) Field of Classification Search
CPC . A61C 17/02; A61C 17/0202; A61C 17/0211; A61C 17/0214; A61C 17/208;
(Continued)

(56) References Cited

U.S. PATENT DOCUMENTS

| 683,075 A | 9/1901 | Schneider |
| 803,475 A | 10/1905 | Dennis |

(Continued)

FOREIGN PATENT DOCUMENTS

| CN | 2536202 Y | 2/2003 |
| EP | 0258512 A1 | 3/1988 |

(Continued)

OTHER PUBLICATIONS

International Report on Patentabililty for PCT/US2017/067792 dated Jul. 9, 2019, 9 pages.

(Continued)

*Primary Examiner* — Justine R Yu
*Assistant Examiner* — Alexander Morales
(74) *Attorney, Agent, or Firm* — Workman Nydegger

(57) ABSTRACT

An oral irrigator has a separate high pressure water system and low pressure mouth rinse system to deliver two different fluids to a pick or other accessories. The water system and mouth rinse system are combined in a handle. The pick is connected to the handle. The water system has a blocking valve located in the handle and the mouth rinse system has a hand pump located in the handle. The hand pump sits next to a valve button for closing the blocking valve. When the hand pump is pressed, it presses against the valve button of the blocking valve to shut off the source of high pressure water to the pick. The pressure in the pick drops so that the hand pump can then introduce mouth rinse into the pick. When the hand pump is released, the blocking valve opens up and high pressure water returns to the pick.

23 Claims, 11 Drawing Sheets

(51) Int. Cl.
　　　*A61C 17/028* 　　(2006.01)
　　　*A61H 13/00* 　　(2006.01)
　　　*A61M 3/02* 　　(2006.01)
　　　*A61C 17/032* 　　(2006.01)

(52) U.S. Cl.
　　　CPC ......... *A61C 17/032* (2019.05); *A61H 13/005* (2013.01); *A61M 3/025* (2013.01); *A61M 2209/086* (2013.01)

(58) Field of Classification Search
　　　CPC .... A61M 1/0064; A61M 3/02; A61M 3/0233; A61M 3/0254; A61M 3/0266; A61H 9/00; A61H 13/00; A61H 13/005; A61H 3/0005
　　　USPC ....... 601/160, 161, 162, 163, 164, 165, 169; 604/74, 80; 137/594, 595, 625.18; 433/74, 80
　　　See application file for complete search history.

(56) References Cited

U.S. PATENT DOCUMENTS

| | | |
|---|---|---|
| 1,500,107 A | 7/1924 | Chandler |
| 1,646,942 A | 10/1927 | Tuorto |
| 1,868,368 A | 7/1932 | Reese |
| 2,672,143 A | 3/1954 | Gold et al. |
| 3,379,192 A | 4/1968 | Warren, Jr. |
| 3,424,156 A | 1/1969 | Smith |
| 3,468,306 A | 9/1969 | Heitzman |
| 3,480,008 A | 11/1969 | Chao |
| 3,481,329 A | 12/1969 | Warren, Jr. |
| 3,489,141 A | 1/1970 | Warren, Jr. |
| 3,504,666 A | 4/1970 | Vireno |
| 3,509,874 A | 5/1970 | Stillman |
| 3,516,402 A | 6/1970 | Toth |
| 3,527,218 A | 9/1970 | Westine |
| 3,537,444 A | 11/1970 | Garn et al. |
| 3,542,017 A | 11/1970 | Adams |
| 3,566,869 A * | 3/1971 | Crowson ............ A61C 17/0211 433/80 |
| 3,568,667 A | 3/1971 | Krieger et al. |
| 3,593,707 A | 7/1971 | Pifer |
| 3,612,045 A | 10/1971 | Dudas et al. |
| 3,669,101 A | 6/1972 | Kleiner |
| 3,731,675 A | 5/1973 | Kelly |
| 3,742,942 A * | 7/1973 | Westline ............ A61C 17/0211 433/216 |
| 3,753,435 A | 8/1973 | Blasnik |
| 3,769,976 A | 11/1973 | Victory |
| 3,769,977 A | 11/1973 | Victory |
| 3,820,532 A | 6/1974 | Eberhardt |
| 3,883,074 A | 5/1975 | Lambert |
| 3,973,558 A | 8/1976 | Stouffer et al. |
| 4,043,337 A | 8/1977 | Baugher |
| 4,106,501 A | 8/1978 | Ozbey et al. |
| 4,122,845 A | 10/1978 | Stouffer et al. |
| 4,164,940 A | 8/1979 | Quinby |
| 4,265,229 A | 5/1981 | Rice et al. |
| 4,564,005 A | 1/1986 | Marchand et al. |
| 4,630,629 A | 12/1986 | Nimberger |
| 4,640,462 A | 2/1987 | Stearns, III |
| 4,793,331 A | 12/1988 | Stewart |
| 4,863,302 A | 9/1989 | Herzfeld |
| 4,865,021 A | 9/1989 | Siderman |
| 4,941,459 A | 7/1990 | Mathur |
| 5,027,798 A | 7/1991 | Primiano |
| 5,095,893 A | 3/1992 | Rawden, Jr. |
| 5,104,315 A | 4/1992 | McKinley |
| 5,136,128 A | 8/1992 | Thomas |
| 5,218,956 A | 6/1993 | Handler et al. |
| 5,220,914 A | 6/1993 | Thompson |
| 5,292,074 A | 3/1994 | Clark et al. |
| 5,365,624 A | 11/1994 | Berns |
| 5,387,182 A | 2/1995 | Otani |
| 5,401,000 A * | 3/1995 | Tsay ............... F16L 37/38 251/149.6 |
| 5,484,281 A | 1/1996 | Renow et al. |
| 5,564,629 A | 10/1996 | Weissman |
| 5,626,472 A | 5/1997 | Pennetta |
| 5,667,483 A | 9/1997 | Santos |
| 5,746,595 A | 5/1998 | Ford |
| 6,089,865 A | 7/2000 | Edgar |
| 6,193,512 B1 | 2/2001 | Wallace |
| 6,305,617 B1 | 10/2001 | Yu |
| 6,602,071 B1 * | 8/2003 | Ellion ............... A46B 11/063 132/322 |
| 6,795,981 B2 | 9/2004 | Sato et al. |
| 6,893,259 B1 | 5/2005 | Reizenson |
| 6,908,047 B2 | 6/2005 | Saunders et al. |
| 7,314,456 B2 | 1/2008 | Shaw |
| D565,175 S | 3/2008 | Boyd et al. |
| 7,367,803 B2 | 5/2008 | Egeresi |
| D574,952 S | 8/2008 | Boyd et al. |
| 7,814,585 B1 | 10/2010 | Reich |
| 8,137,295 B2 | 3/2012 | Castaldi et al. |
| 8,444,340 B2 | 5/2013 | Best |
| 8,449,295 B2 | 5/2013 | Hegemann |
| 8,540,660 B2 * | 9/2013 | Martin ............ A61M 16/0006 604/24 |
| 8,647,447 B2 | 2/2014 | Bunting et al. |
| 8,684,956 B2 | 4/2014 | McDonough et al. |
| 8,801,316 B1 | 8/2014 | Abedini |
| D725,770 S | 3/2015 | Kim et al. |
| D728,118 S | 4/2015 | Welt et al. |
| D747,464 S | 1/2016 | Taylor et al. |
| D755,985 S | 5/2016 | Porat |
| D802,119 S | 11/2017 | Kim |
| 2003/0181837 A1 | 9/2003 | Kaplowitz |
| 2004/0045107 A1 | 3/2004 | Egeresi |
| 2006/0057539 A1 | 3/2006 | Sodo |
| 2006/0079818 A1 | 4/2006 | Yande |
| 2007/0184404 A1 | 8/2007 | Johnki |
| 2008/0078021 A1 | 4/2008 | Welch |
| 2009/0082706 A1 | 3/2009 | Shaw |
| 2009/0098506 A1 | 4/2009 | Shaw |
| 2009/0124945 A1 | 5/2009 | Reich et al. |
| 2012/0064480 A1 | 3/2012 | Hegemann |
| 2014/0261534 A1 | 9/2014 | Schepis |
| 2015/0072303 A1 | 3/2015 | Boyd et al. |
| 2015/0102130 A1 | 4/2015 | Davenport |
| 2015/0250570 A1 | 9/2015 | Persons et al. |
| 2016/0151133 A1 | 6/2016 | Luettgen et al. |

FOREIGN PATENT DOCUMENTS

| | | |
|---|---|---|
| FR | 2277567 | 2/1976 |
| JP | 2006141613 A | 6/2006 |
| JP | 2006141913 A | 6/2006 |
| KR | 200374492 Y1 | 1/2005 |
| KR | 20120126260 A | 11/2012 |
| WO | 2004021958 A1 | 3/2004 |

OTHER PUBLICATIONS

Pneumadyne, Inc. Cross Section, 2-Way Normally Open, Nov. 28, 2016.
Pexco Medical, Multi-Lumen Tubing, www.pexco.com/medical, Nov. 28, 2016.
Pneumadyne, Bleed Values, last viewed Oct. 25, 2016.
Dental Depot, Showerfloss, https://www.dentaldepot.com/product/SHOWER_FLOSS/SHOWERFLO, last viewed Nov. 11, 2016.
Waterpik Showerpik Water Flosser (WP-480), www.amazon.com, last viewed Mar. 4, 2016.
Hydraulics & pneumatics, Sorting through pneumatic directional control valves, dated Apr. 1, 1997.
Standard Push Button Value Drawing, Nov. 28, 2016.
Versa, Series B Valves, Air Valves for Industry Since 1949, Bulletin B-2011, www.versa-valves.com, Nov. 28, 2016.
The Waterpik® White Ultra Water Flosser WP-100, https://www.waterpik.com/oral-health/products/dental-water-flosser/WP-100/, last viewed Nov. 11, 2016.

(56) References Cited

OTHER PUBLICATIONS

Mouthwash & Your Waterpik® Water Flosser, dated Jun. 12, 2015, https://www.waterpik.com/oral-health/blog/waterpik-mouthwash/, last viewed Nov. 4, 2016.

Wikipedia.com, Gingivitis, https://en.wikipedia.org/wiki/Gingivitis, last viewed Mar. 4, 2016.

Wikipedia.com, Oral irrigator, https://en.wikipedia.org/wiki/Oral_irrigator, last viewed Mar. 4, 2016.

English Translation FR2277567 Jean Baptiste published Feb. 6, 1976.

KleenTeeth DenTrust 3-Sided Toothbrush—Soft http://www.kleenteeth.com/dentrust-3-sided-toothbrush-soft/?gclid=CLr8, last viewed Dec. 19, 2016.

International Search Report from PCT Application No. PCT/US2017/067792, dated Apr. 16, 2018.

* cited by examiner

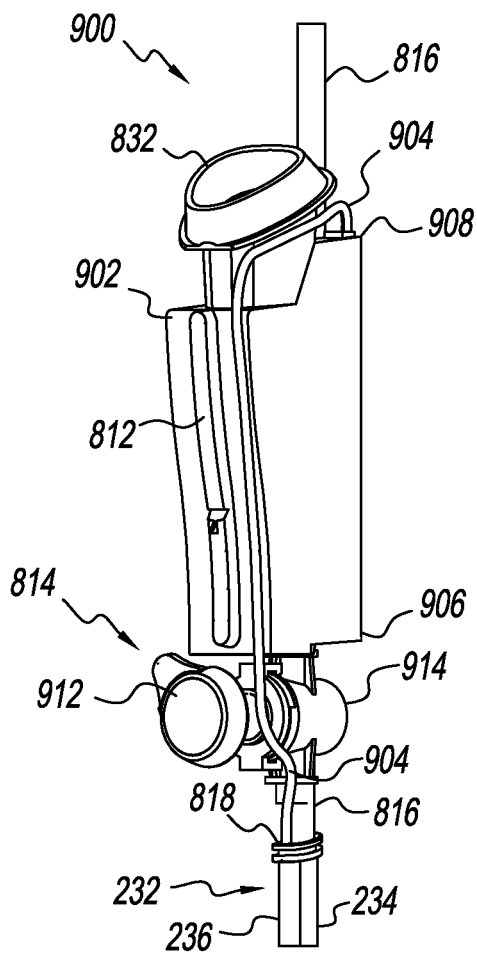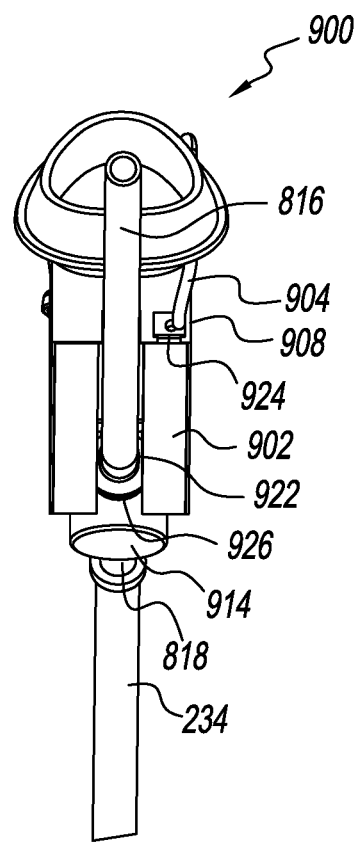
FIG. 9A
FIG. 9B

ORAL IRRIGATOR

COPYRIGHT AND TRADEMARK NOTICE

A portion of the disclosure of this patent document contains material to which a claim for copyright is made. The copyright owner has no objection to the facsimile reproduction by anyone of the patent document or the patent disclosure, as it appears in the Patent and Trademark Office patent file or records, but reserves all other copyright rights whatsoever.

FIELD OF THE INVENTION

Embodiments of the present invention relate to teeth and gum cleaning devices.

BACKGROUND OF THE INVENTION

Current designs for oral irrigators combine mouth rinses with water in a common reservoir and use an electrically driven pump to deliver the mixture at high pressure to a pick. The high pressure flow may be a pulsatile flow. A user places the pick in said user's mouth to clean said user's teeth and irrigate said user's gums. There is need, however, for an oral irrigator that can deliver full strength mouth rinse to a user's mouth without dilution and high pressure, pulsatile, cleaning water to a user's mouth without requiring the use of an electric pump.

SUMMARY OF THE INVENTION

The summary of the invention is provided as a guide to understanding the invention. It does not necessarily describe the most generic embodiment of the invention or the broadest range of alternative embodiments.

An improved oral irrigator comprises a high pressure water delivery system in parallel with a low pressure mouth rinse delivery system to alternatively deliver said fluids to a common pick. The water delivery system provides water from a source of high pressure water such as a shower head. The mouth rinse delivery system provides mouth rinse from a source of low pressure mouth rinse, such as a reservoir. Both systems are combined in a handle that a user holds. The pick is attached to the handle. The user irrigates said user's teeth and gums by placing the pick in said user's mouth and manipulating it using the handle. As used herein, a "pick" is any device with a fluid inlet and a fluid outlet. It includes conical tubes with a large inlet and small outlet, T devices with multiple fluid outlets, and devices with brushes, such as a toothbrush with a fluid inlet in the handle and one or more fluid outlets in the brush. The tooth brush may have multiple heads for simultaneously cleaning the tops and sides of teeth.

The water delivery system in the handle comprises a blocking valve with a spring loaded valve button. The spring loaded valve button is biased normally open. When the spring loaded valve button is depressed, the blocking valve and hence the high pressure water is shut off to the pick. This drops the pressure in the pick and allows low pressure mouth rinse to be pumped into the pick with a hand pump that is also in the handle. This also enables the user to turn off the high pressure water to the pick when entering or removing the pick from the mouth. When the user is done pumping mouth rinse into the pick, the spring loaded valve button in the blocking valve is released, the blocking valve opens up, and high pressure water is then reintroduced into the pick. A pressure oscillator may be present in the handle to cause the high pressure water to oscillate in pressure and thus provide a pulsing action to the user's teeth and gums. The pick may have a single exit orifice or may have multiple exit orifices.

The mouth rinse delivery system comprises a hand pump mounted in the handle. The hand pump is used to pump mouth rinse from a reservoir into the pick. Mouth rinse can be any fluid a user might want to introduce into said user's mouth. This includes Listerine® mouthwash, prescription mouth rinses such as chlorhexidine, teeth whitening agents, essential oils and saline rinses. The hand pump has a spring loaded piston that is biased to a normally expanded configuration. As used herein, "spring loaded piston" refers to any compressible chamber that will have a restoring force once compressed. This includes, for example, a thick walled elastomeric bladder. A pump button is attached to the spring loaded piston so that a user can compress the piston by hand and thus pump mouth rinse into the pick. In particular, the pump button is positioned and dimensioned to be pressed by a person's thumb.

The hand pump inside the handle is mounted adjacent to the blocking valve inside the handle such that the valve button on the blocking valve will be pressed in and close the blocking valve when a user puts pressure on the pump button of the hand pump. When the blocking valve closes, the high pressure water is disconnected from the pick. The pressure in the pick drops and allows the user to pump mouth rinse into the pick using the hand pump. When the user releases the pump button, the blocking valve opens and high pressure water is again delivered to the pick.

There is an outlet check valve attached to the outlet of the spring loaded piston to prevent high pressure water in the pick from back flowing into the hand pump. There is also an inlet check valve mounted to the inlet of the spring loaded piston to prevent mouth rinse from back flowing into the reservoir when the pump button is pressed. The inlet valve or the outlet valve may be spring loaded pressure relief valves that require a positive pressure to open. This will prevent siphoning of mouth rinse through the system.

The mouth rinse reservoir may be housed in a console mounted on the wall of a shower. High pressure water may be piped from the shower head and through the console. A dual lumen flexible supply tube may separately convey low pressure mouth rinse and high pressure water from the console to the handle. A mount may be provided on the console for holding the handle when the handle is not in use. The mount is dimensioned to hold the exit orifice of the pick above the top of the mouth rinse reservoir so that mouth rinse will not siphon out of the reservoir when the handle is stored on the console.

BRIEF DESCRIPTION OF DRAWINGS

FIG. 9A is a rendering of the console of FIG. 8A with the housing removed to show the mouth rinse reservoir inside.

FIG. 9B is a rendering of the console of FIG. 9A from a top rear perspective.

DETAILED DESCRIPTION

The detailed description describes non-limiting exemplary embodiments. Any individual features may be combined with other features as required by different applications for at least the benefits described herein.

As used herein, the term "about" means plus or minus 10% of a given value unless specifically indicated otherwise.

As used herein, the term "shaped" means that an item has the overall appearance of a given shape even if there are minor variations from the pure form of said given shape.

Figure 1:
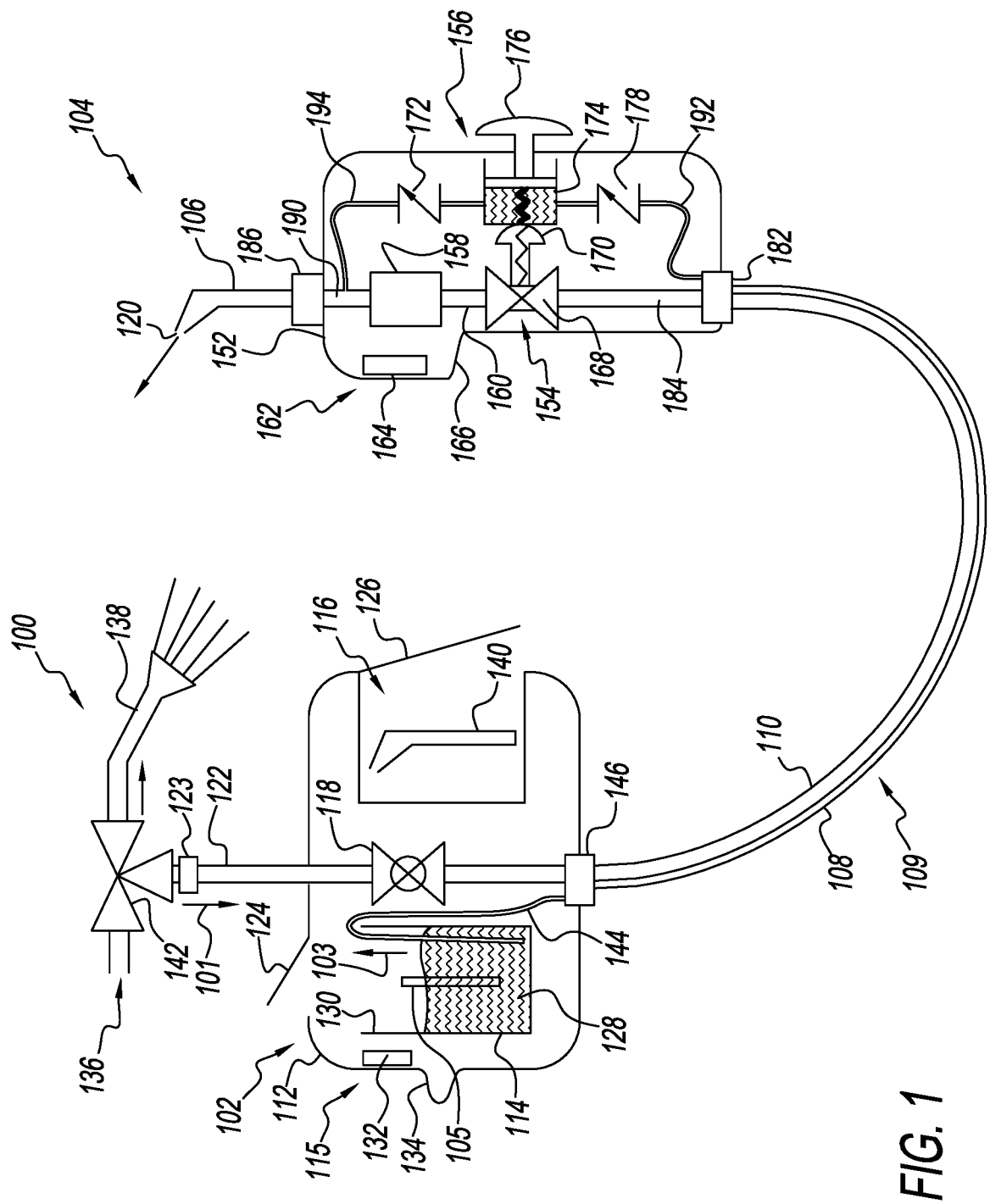
FIG. 1 is a schematic of an oral irrigator.

FIG. 1 is a schematic of an oral irrigator 100. The oral irrigator comprises a high pressure water delivery system 101 and a low pressure mouth rinse delivery system 103. Both systems are housed in part in a console 102 and an attached handle 104. Attachment is by a flexible supply tube 109.

Console

The water delivery system comprises a water supply tube 122. This conveys high pressure water from a source of high pressure water 136, such as the piping leading into a shower head 138. A three way valve 142 may be provided to redirect high pressure water from the shower head to the water delivery system. Any source of high pressure water may be used, such as an electrically driven pump. The water should have a minimum pressure of 10 psig. 40 to 60 psig is suitable. An electrically driven pump may be provided to boost and control the pressure of the water from the high pressure source. The electrically driven pump may be battery operated. A pressure regulator may be provided to reduce and control the pressure from the high pressure source of water. A pressure regulator may be needed if the source of high pressure water is 100 psig or more. A filter 123, such as a screen, may be provided in the water supply tube to remove particulates from the supply water.

The water supply tube proceeds into and through the console. The console may be mounted on the wall of a shower. Any mounting means may be used. The console may be mounted in any convenient location such as next to a sink. A shut off valve 118 may be provided in the water supply tube and as part of the console. A user can turn the high pressure water on or off using the shut off valve. The user can also regulate the flow of high pressure water to an intermediate value by partially closing the shut off valve. The water supply tube may be connected to a console bulkhead fitting 146 at about the bottom of the console. The attachment of tubes to bulkhead fittings may be permanent or removable (e.g. insert fittings). The flexible supply tube may connect to the console bulkhead fitting and convey both high pressure water and low pressure mouth rinse to the handle as separate streams. The flexible supply tube may be a dual lumen tube. The first lumen 110 of said dual lumen tube may have a relatively large internal diameter and connect to the water supply tube via said console bulkhead fitting. A relatively large diameter minimizes the pressure drop of the high pressure water as it passes through the first lumen. A suitable internal diameter is 3 mm or greater. A suitable diameter may further be in the range of 4.5 to 7.5 mm. The flexible supply tube can be any length suitable for conveying high pressure water from the console to the handle. A suitable length is in the range of 0.5 to 2 meters. A suitable length is about 1 meter.

The console may comprise a reservoir 114 for holding a volume of mouth rinse 128. Mouth rinse may be any fluid suitable for introduction into a person's mouth. The reservoir may have an open top 130 and thus be at about atmospheric pressure. A mouth rinse tube 144 may proceed from inside the reservoir at about its bottom, over about the top of the reservoir, and then outside of the reservoir and down to the console bulkhead fitting. The mouth rinse tube may then be connected to the second lumen 108 of the flexible supply tube. The internal diameter of the second lumen may be small relative to the internal diameter of the first lumen. This keeps the volume of the second lumen small so that a user does not have to pump a hand pump 156 in the handle many times in order to deliver mouth rinse to a pick 106. A suitable diameter for the second lumen is 4 mm or less. A suitable diameter may be in the range of 2.75 mm to 3.25 mm.

The lumens in the flexible supply tube do not have to be circular in cross section. They can be any suitable shape. Suitable dimensions for the noncircular lumens can be calculated from the corresponding suitable diameters of the circular lumens described herein using standard fluid mechanical calculations related to volume in a tube and/or pressure drop versus flow.

The console may comprise a console mount 115. This will be mated to a handle mount 162 on the handle. The combined mounts will hold the handle in a storage position when not in use. The console mount may comprise a magnet 132 and a shelf 134. The handle mount may comprise a magnet 164 and an overhang 166. The magnets, shelf and overhang align so that the overhang sits on the shelf and the magnets are about opposite of each other and urge towards each other when the handle is mounted on the console. The shelf height is set so that the exit orifice 120 of the pick is above the top of the reservoir 130. This will prevent mouth rinse from siphoning through the mouth rinse delivery system when the handle is stored on the console.

The console may have a housing 112. A cover 124 may be provided in the console housing and above the top of the reservoir to prevent shower water or other materials from entering the reservoir. The cover may be hinged to allow easy opening and refilling of the reservoir. A level gauge 105 may be provided so that the user can see when the reservoir needs to be refilled.

A storage chamber 116 may be provided in the console. The storage chamber may be used to store one or more additional picks 140. The additional picks may be used by different people that use the oral irrigator. The picks may be color coded. A door 126 may be provided in the console housing to cover the storage chamber.

Handle

The flexible supply tube conveys high pressure water and low pressure mouth rinse to the handle 104. The flexible supply tube may connect to a bottom bulkhead fitting 182 in the bottom of the handle. The first lumen of the flexible supply tube connects to an inlet water tube 184 in the handle. The inlet water tube connects to the inlet of a blocking valve 154 mounted in the handle. The outlet of the blocking valve connects to an outlet water tube 160. The outlet water tube may connect to the inlet of an optional pressure oscillator 158. The outlet of the pressure oscillator 190 connects to a top bulkhead fitting 186 in about the top of the handle. The pick 106 connects to the top bulkhead fitting. A releasable connection may be provided in the top bulkhead fitting to hold the pick in place and then release it as needed. The releasable connection may be a quick disconnect that can be operated by hand.

The blocking valve comprises a body 168 and a spring loaded valve button 170. The handle may comprise a housing 152. The body of the blocking valve may rest against the housing of the handle so that it is held firmly in place when pressure is placed on the spring loaded valve button. The spring loaded valve button is biased normally open. When the button is pressed, the blocking valve closes. When the button is released, the blocking valve opens.

The second lumen in the flexible supply tube is connected through the bottom bulkhead fitting of the handle to a flexible inlet mouth rinse tube 192. The inlet mouth rinse tube connects to an inlet check valve 178 of the hand pump 156. The hand pump comprises the inlet check valve, a spring loaded piston 174, a pump button 176 and an outlet check valve 172. The outlet check valve connects to a flexible outlet mouth rinse tube 194. The outlet mouth rinse tube connects to the oscillator outlet 190.

The hand pump is flexibly mounted inside the handle housing and adjacent to the blocking valve so that when the pump button is pressed and lateral force is placed on the spring loaded piston, the spring loaded piston can move laterally and provide force on the valve button and thus close the blocking valve. When the blocking valve is closed, the high pressure water in the pick drains out and the pressure in the oscillator outlet drops. The spring loaded piston can then compress under the hand force placed on the pump button and mouth rinse is pumped into the oscillator outlet and hence into the pick. When the pump button is released, the valve button on the blocking valve returns to its open position and high pressure water flows back into the pick.

The outlet check valve in the hand pump is biased away from the spring loaded piston so that said outlet check valve prevents high pressure water in the oscillator outlet from back flowing into the hand pump. The inlet check valve on the hand pump is biased into the spring loaded piston so that mouth rinse does not back flow into the reservoir when said spring loaded piston is compressed.

The pressure oscillator 158 may be any device that causes fluctuations in the pressure of the water flowing into the pick. This includes mechanical devices, electrically powered devices, and fluidic devices. An exemplary turbine based pressure oscillator is described herein with reference to FIGS. 6 and 7.

Exemplary Handle

Figure 2:
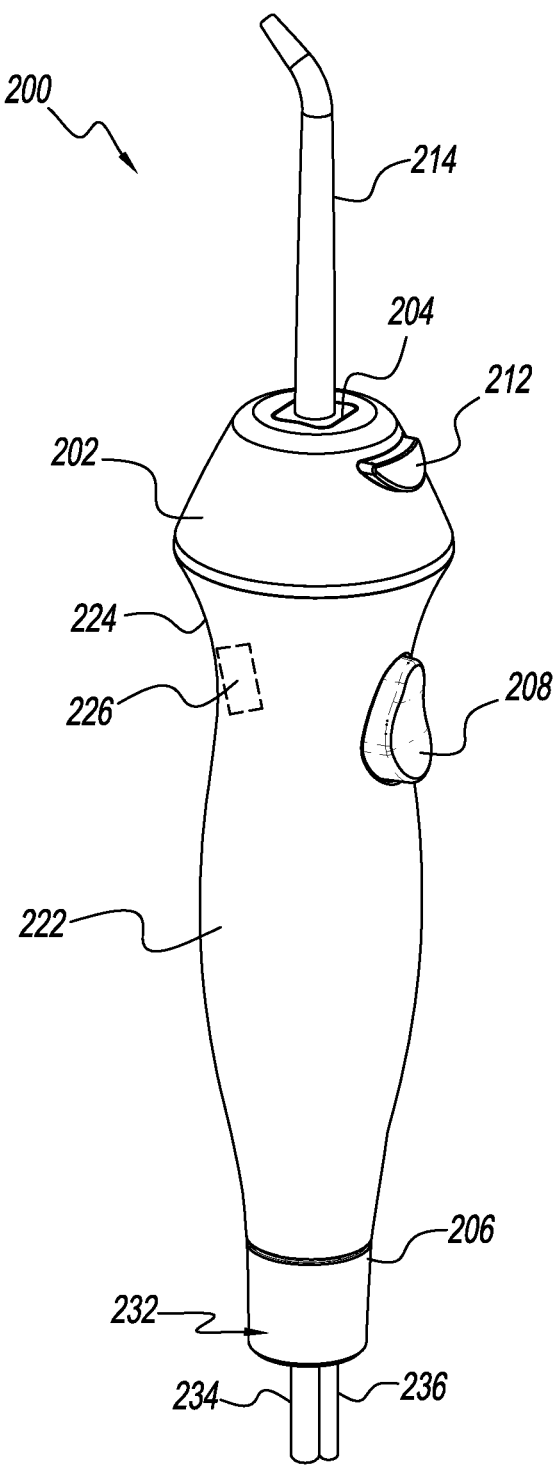
FIG. 2 is a rendering of an exemplary handle.

FIG. 2 is a rendering of an exemplary handle 200. The handle comprises a top bulkhead fitting 204, a housing 202, and a bottom bulkhead fitting 206. The housing is shaped to provide an overhang 224 above a bulge 222. This provides a grip for a user that will be secure even if the user has a slippery hand due to, for example, use in a shower. The overhang forms part of a handle mount. A magnet 226 may be provided inside the housing and underneath the overhang to mate with a corresponding magnet in a console.

A pick button 212 may be provided so that a pick 214, may be held in place in the top bulkhead fitting. When the pick button is depressed, the pick is released.

A pump button 208 may protrude out of the housing so that a user may depress the pump button and pump mouth rinse into the pick as described above.

The bottom bulkhead fitting may be adapted to receive an end of a dual lumen flexible supply tube 232. The flexible supply tube may comprise a first lumen 234 for conveying high pressure water and a second lumen 236 for conveying low pressure mouth rinse.

Figure 3A:
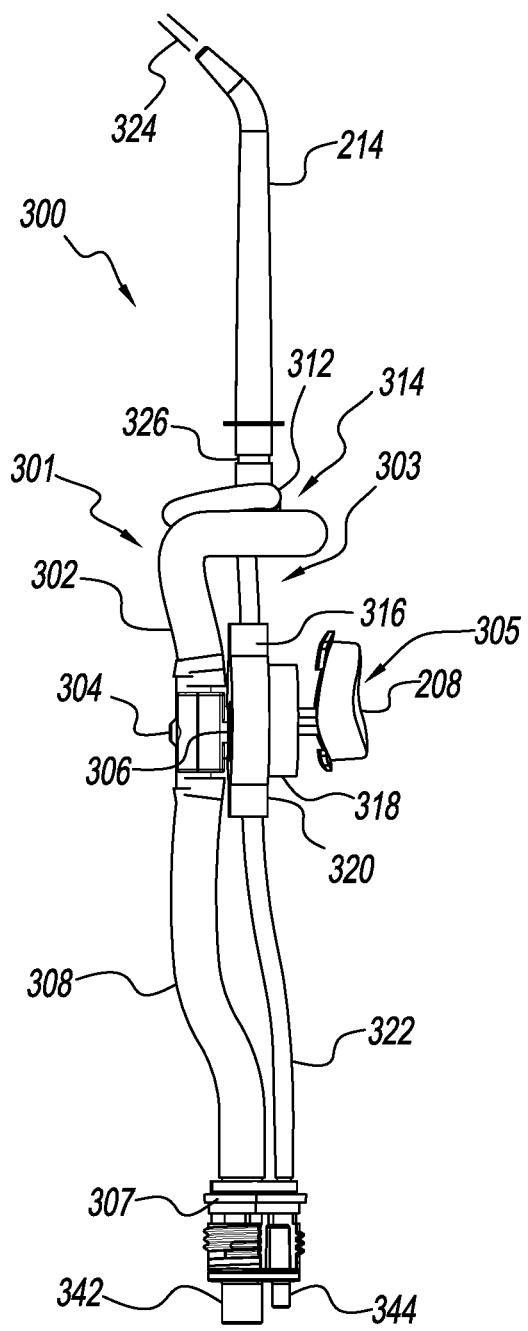
FIG. 3A is a rendering of the handle of FIG. 2 with the housing removed so the internal fluid systems can be seen.

FIG. 3A is a rendering 300 of the handle of FIG. 2 with the housing removed so that the internal fluid systems can be seen. The internal fluid systems comprise portions of the water delivery system 301 and mouth rinse delivery system 303. The water delivery system in the handle comprises a first lumen 342 in the bottom bulkhead fitting 307 (cover removed), a water inlet tube 308, a blocking valve 304 comprising a valve button 306, a water outlet tube 302 and a pressure oscillator 314. The pressure oscillator is hidden by the water outlet tube in the view presented in FIG. 3A. It is visible at item 314 in FIG. 5. The pick 214 is shown mounted in the outlet of the pressure oscillator with the top bulkhead fitting that holds the pick in place rendered invisible. A pick exit orifice 324 is shown at the distal tip of the pick. A pick inlet 326 is shown at the proximal end of the pick.

The mouth rinse delivery system in the handle comprises a second lumen 344 in the bottom bulkhead fitting, an inlet mouth rinse tube 322, a hand pump 305 and an outlet mouth rinse tube 312. The hand pump comprises an inlet check valve 320, a spring loaded piston 318, the pump button 208, and an outlet check valve 316. The hand pump is flexibly mounted inside the handle with its bottom located on the top of the valve button of the blocking valve. The blocking valve rests against the handle housing (item 202, FIG. 2) so that the blocking valve will firmly mounted in place and the valve button can be depressed when the pump button on the hand pump is pressed and the bottom of the spring loaded piston is pushed down.

Figure 3B:
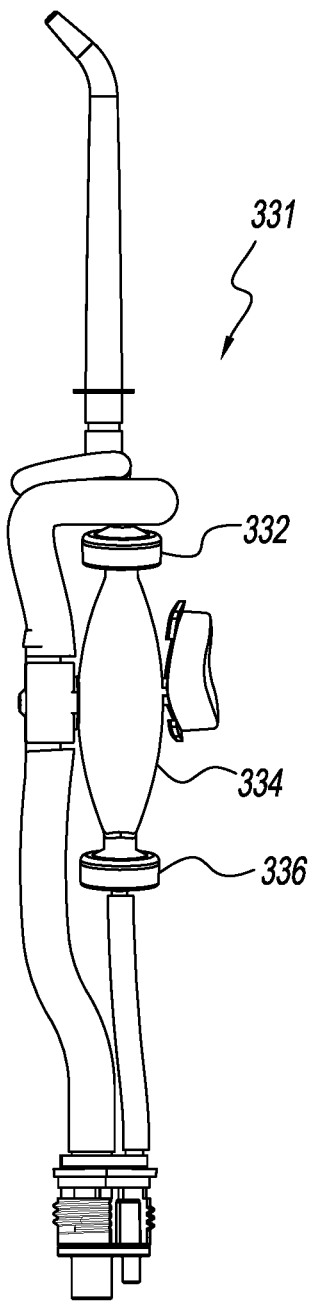
FIG. 3B is a rendering of a handle similar to the handle of FIG. 3A except the spring loaded piston is shown as an elastomeric bladder.

FIG. 3B is a rendering of a handle 331 similar to the handle 300 of FIG. 3A except the spring loaded piston is shown as an elastomeric bladder 334. The outlet check valve 332 and inlet check valve 336 are shown as flap valves.

Figure 4:
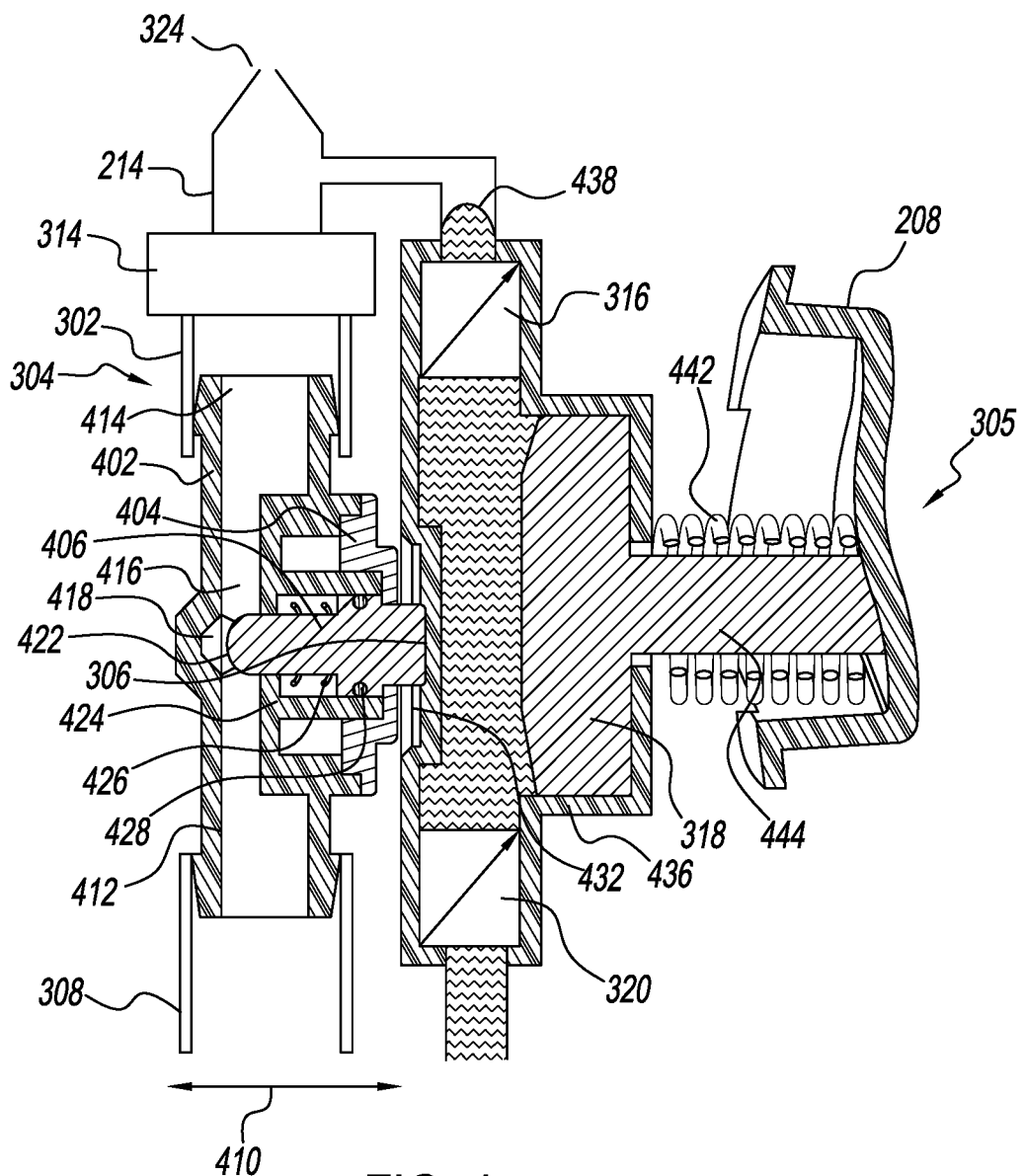
FIG. 4 is a cut away side view of the blocking valve of FIG. 3A in combination with the hand pump of FIG. 3A.

FIG. 4 is a cut away side view of the blocking valve 304 of FIG. 3A in combination with the hand pump 305 of FIG. 3A. The pick 214, pressure oscillator 314, outlet water tube 302, and inlet water tube 308 are shown schematically.

The blocking valve comprises a body 402, a cap 404, and a spring loaded valve button 306. The body comprises an inlet 412, an internal channel 416, a lateral bore 424 at right angles to the internal channel, and an outlet 414. The spring loaded valve button comprises a shaft 406, a spring 426 and a distal tip 422.

The inlet and outlet of the blocking valve are collinear so that pressurized water can flow from the bottom of the handle up to the pick mounted in the top of the handle. The collinearity of the inlet and outlet helps keep the width 410 of the blocking valve to less than twice the diameter of the inlet water tube or outlet water tube. This helps keep the overall width of the handle small enough to fit in a person's hand. A suitable width of the blocking valve is 12.5 mm. A suitable outer diameter of the inlet water tube is 8.5 mm. A suitable ratio of the width of the blocking valve to the outer diameter of the inlet water tube is 1.5 or less.

The valve button is mounted horizontally in the bore of the valve body. The spring 426 surrounds the shaft of the valve button. The spring is normally compressed so that it biases the valve button out. A seal 428, such as an O ring, may be provided to make the spring loaded valve button water tight against the bore. The cap 404 may screw onto, snap onto, press fit onto or otherwise attached to the valve body to hold the valve button in the bore.

The tip of the valve button may partially extend into the internal channel of the valve body. 1 mm is a suitable extension for a diameter of the internal channel of 2 mm. A recessed seat 418 may be provided in the internal channel and opposite the tip of the valve button. When the valve button is pressed in, the tip proceeds across the rest of the internal channel and into the seat to seal off said internal channel. The outer diameter of the shaft should be larger than the internal diameter of the internal channel so that it completely blocks the internal channel when the blocking valve is closed. A suitable outer diameter of the shaft is 3 mm when the internal diameter of the internal channel is 2 mm.

In order to keep the width of the blocking valve small, the diameter of the internal channel has to be small so that the tip of the valve button does not have to travel far to close the blocking valve. This helps keep the length of the valve button that extends above the top of the cap small. A suitable diameter of the internal channel is 2 mm.

A suitable internal diameter of the inlet and outlet of the blocking valve is about 4.5 mm. It is surprising that the diameter of the internal channel can be less than ½ of the diameter of the inlet or outlet. Normally this would produce an unacceptable pressure drop in a general purpose blocking valve. In the applications described herein, however, small diameter of the internal channel is acceptable due in part to the even smaller diameter of the exit orifice 324 in the pick. A suitable diameter of the exit orifice is in the range of 0.45 to 0.6 mm. This is required to get maximum velocity in the high pressure water exiting the pick without causing atomization. Thus most of the pressure drop of the high pressure water flowing through the handle occurs at the exit orifice of the pick where it translates to a high velocity water jet for cleaning teeth.

The hand pump 305 in FIG. 4 comprises an outlet check valve 316 (shown schematically), a cylinder 436, a spring loaded piston 318 and an inlet check valve 320 (shown schematically). The piston is mounted within the cylinder. A piston shaft 444 and piston spring 442 (shown schematically) extend laterally from the piston and are mounted to the pump button 208. A recess 432 is provided in the bottom of the cylinder. The valve button of the blocking valve is located in the recess. The recess may be large enough to fit over the top of the cap of the blocking valve.

A leading edge of mouth rinse 438 is shown emerging from the outlet check valve when the pump button is pressed, the blocking valve is closed, and mouth rinse is pumped to the pick. The outlet of the hand pump is connected to the outlet of the pressure oscillator and hence to the inlet of the pick.

Figure 5:
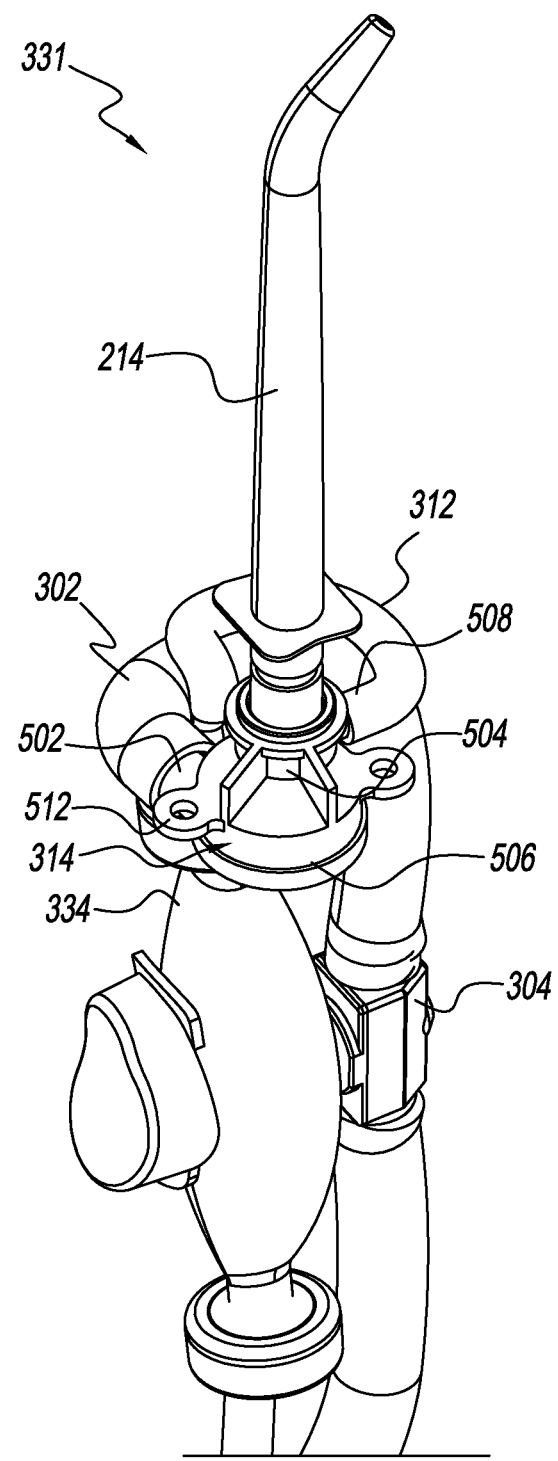
FIG. 5 is a rendering of the handle of FIG. 3B from a top perspective so that a pressure oscillator in the handle is visible.

FIG. 5 is a rendering of the handle 331 of FIG. 3B with the pressure oscillator 314 visible. The blocking valve 304 and elastomeric bladder 334 are also shown. The pressure oscillator comprises an oscillator inlet 502, an oscillator outlet 504, a turbine housing 506, one or more mounting tabs 512 and a mouth rinse port 508. The outlet water tube 302 proceeds from the blocking valve and is bent to introduce high pressure water into the oscillator horizontally into the turbine housing. The oscillator outlet proceeds upwards from the top of the turbine housing where it connects to the pick 214. The outlet mouth rinse tube 312 proceeds up from the elastomeric bladder and connects horizontally to the mouth rinse port. The mouth rinse port is connected to the oscillator outlet. Thus in operation, only water proceeds through the pressure oscillator. This minimizes clogging that might occur due to chemicals or other materials that may be present in the mouth rinse. It also reduces the hand pressure required to pump mouth rinse into the pick.

Figure 6:
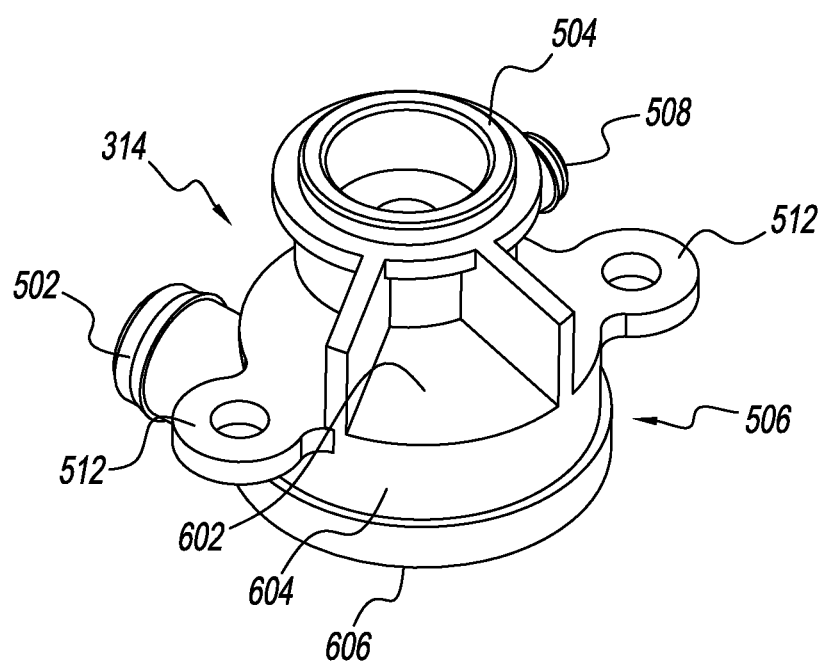
FIG. 6 is a rendering of the pressure oscillator of FIG. 5.

FIG. 6 is a rendering of the pressure oscillator 314 of FIG. 5. The oscillator inlet 502, oscillator outlet 504, turbine housing 506 mouth rinse port 508 and mounting tabs 512 can be seen. The turbine housing comprises a top 602, side wall 604 and bottom 606.

Figure 7:
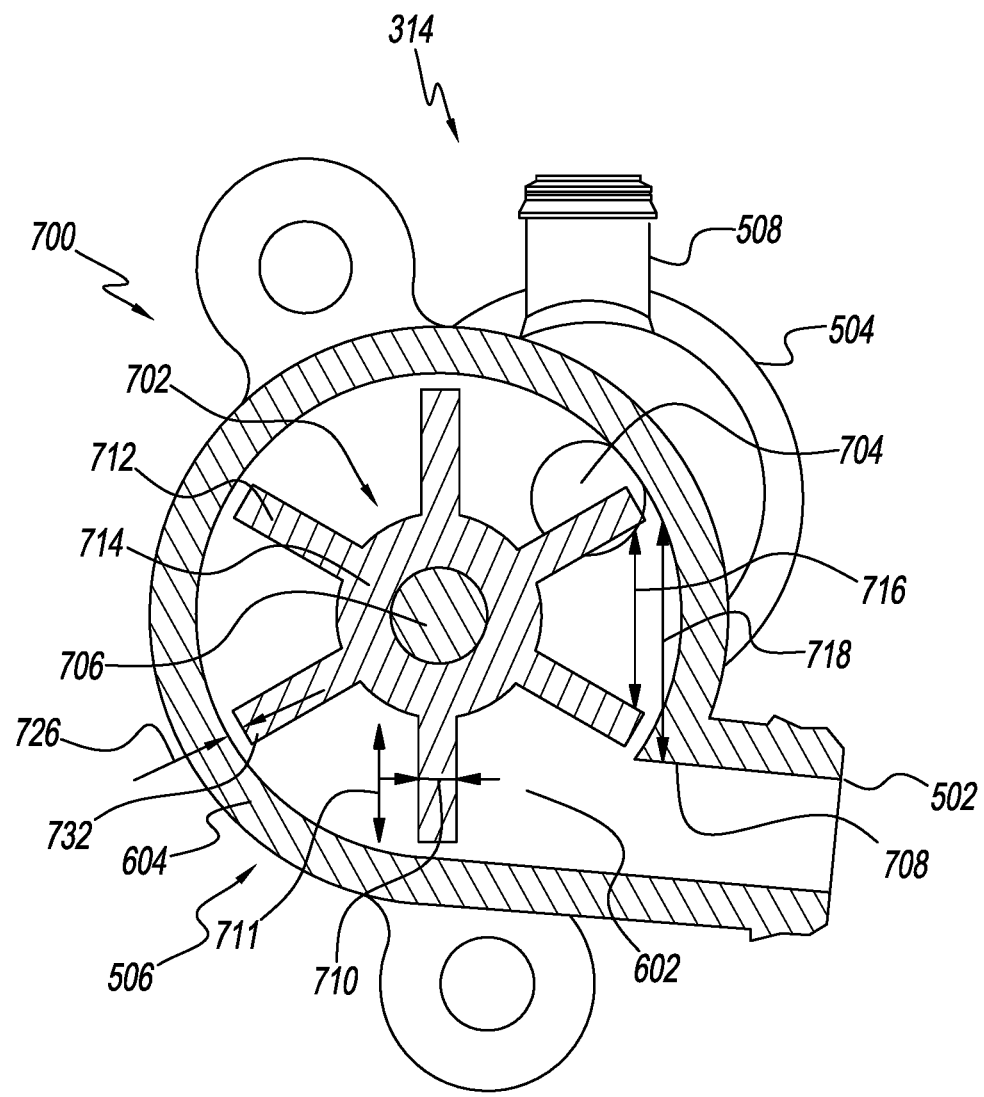
FIG. 7 is a cut away bottom view of the pressure oscillator of FIG. 5 showing an internal turbine wheel.

FIG. 7 is a cut away bottom view of the pressure oscillator 314 of FIG. 5. The oscillator inlet 502, oscillator outlet 504, and mouth rinse port 508 can be seen. The pressure oscillator comprises a turbine 700. The turbine comprises a turbine housing 506 and a turbine wheel 702. The turbine housing comprises a top 602, a side wall 604 and a bottom (item 606, FIG. 6). The turbine wheel comprises a hub 714, and a plurality of vanes 712. The turbine side wall has a generally circular horizontal cross section. A turbine inlet 708 introduces high pressure water into the housing from the oscillator inlet in a direction that is generally tangential to the side wall.

A turbine outlet 704 is located in the turbine top. The turbine outlet allows water to flow from the turbine into the outlet of the pressure oscillator. The mouth rinse port 508 is downstream of the turbine outlet.

The turbine housing comprises a vertical axle 706 located at about the center of the circular cross section of the side wall. The vertical axle can be attached to either the top of the turbine housing or the bottom. The hub of the turbine wheel sits on the axle. The turbine vanes proceed radially from the hub. They are spaced regularly on the hub. Each vane has a distal tip 732. There is a gap 726 between the distal tips of the vanes and the side wall. Each vane is described by a width 710 and a length 711.

In operation, high pressure water flows into the turbine inlet and causes the turbine wheel to spin. The high pressure water then flows out of the turbine outlet. When the vanes sweep past the turbine outlet, the outlet is partially blocked. This causes pressure fluctuations in the high pressure water flowing out of the turbine outlet and into the pick. A suitable width of the vanes is 1 mm or greater for a turbine outlet diameter of about 3 mm. The diameter of the side wall is about 13 mm. It has been found by experiment that a relatively wide gap of 0.5 mm or greater between the tips of the vanes and the side wall helps the turbine wheel spin freely. A suitable ratio of gap to side wall diameter, therefore, is 0.03 or greater.

A suitable hub diameter is about 5.5 mm. A suitable overall wheel diameter is about 12 mm. 6 is a suitable number of vanes. The turbine outlet should be located far enough away from the turbine inlet so that there is always at least one vane between the inlet and outlet. This will prevent water from flowing directly to the outlet without rotating the vanes. The closest spacing 718 between the turbine inlet and outlet, therefore, should be greater than the spacing 716 between the tips of two adjacent vanes. If the vane tips are spaced 5.5 mm apart, for example, then the closest spacing between the turbine inlet and the turbine outlet should be at least 5.5 mm. A spacing of 5.9 mm is suitable.

Exemplary Console

Figures 8A, 8B:
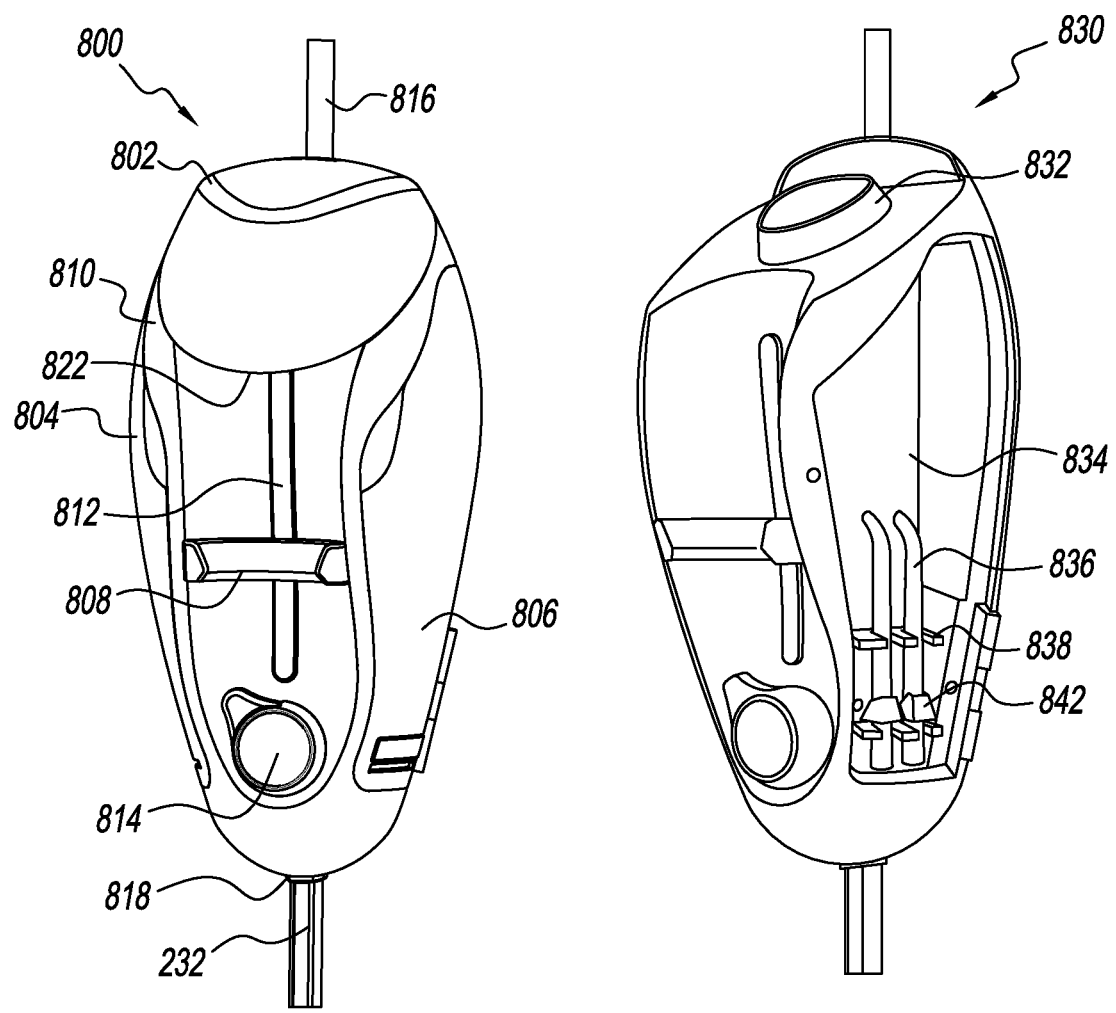
FIG. 8A is a rendering of a console.
FIG. 8B is a rendering of the console of FIG. 8A with the reservoir cover and right storage door removed.

FIG. 8A is a rendering of an exemplary console 800. The console comprises a housing 810, a reservoir for mouth rinse (item 902, FIG. 9A), a reservoir cover 802, a reservoir level gauge 812, a water supply tube 816, a shelf 808, a shut of valve 814, a console bulkhead fitting 818, a left storage door 804 and a right storage door 806. The dual lumen flexible supply tube 232 of FIG. 2 is attached to the bottom of the console bulkhead fitting. The console bulkhead fitting is attached to about the bottom of the console. The water supply tube conveys high pressure water from a source of high pressure water to the console bulkhead fitting. The shut off valve is adapted to close the water supply tube or open it as required. The reservoir cover is attached to the top of the housing with a rear hinge. It overhangs the housing to form an air passage 822 from outside the housing to underneath the cover. This allows air to go into the reservoir when mouth rinse is pumped out. The left side door and right side door are each attached to the back of the housing by a hinge.

The shelf 808 is designed to form a stable cradle for the overhang 224 (FIG. 2) of the handle. As used herein, a stable cradle is a mount that holds an item such that said item is held on said mount by the force of gravity. Said shelf forms a stable cradle for said overhang in part due to said self's arcuate form which wraps in part around the handle underneath the overhang. A magnet may still be provided, for example, in the shut off valve 814 so that the magnet in the handle will urge towards it and increase the stability of the handle being held on the cradle.

FIG. 8B is a rendering 830 of the console of FIG. 8A with the reservoir cover and right storage door removed. A reservoir inlet 832 can be seen. In operation, a user can open the reservoir cover and pour mouth rinse into the reservoir inlet. The cover can then be closed to keep foreign matter, including shower water, from entering the reservoir. The right storage chamber 834 has room for one or more extra picks 836. The picks may be held in place by one or more clips 838. The picks may be color coded 842 so that different colored picks can be assigned to different users. The storage chamber is wider at its top than at its bottom. The top area may have clips or other holders for storing wider picks, such as the massager pick described in FIG. 11. A similar or different structure may be provided in a left storage chamber that is covered by the left storage door.

FIG. 9A is a rendering 900 of the console of FIGS. 8A and 8B with the housing removed. The water supply tube 816, reservoir inlet 832, level gauge 812, shut off valve 814 and console bulkhead fitting 818 (cover removed) are visible. The reservoir 902 can now be seen. The reservoir can be made of any material compatible with mouth rinses. Polyethylene is a suitable material. The material may be at least translucent or transparent so that the level of mouth rinse can be seen in the level gauge. The shape of the reservoir can be adapted to conform to the desired housing shape.

The reservoir comprises a top 908 and a bottom 906. A console mouth rinse tube 904 may proceed from about the bottom of the reservoir to the top of the reservoir and then back down to the console bulkhead fitting. There it is connected to the second lumen 236 of the flexible supply tube 232. An advantage of having the console mouth rinse tube proceed from the bottom of the reservoir to the top of the reservoir is that there is no need for a fitting in the bottom of the reservoir to remove mouth rinse. Said fitting might leak.

The shut off valve comprises a handle 912 and a body 914. The water supply tube connects to the body of the shut off valve and is shut off when the handle is turned. The shut off valve may be a ball valve. The shut off valve may alternatively be a regulating valve in case the pressure delivered to the handle needs to be reduced.

FIG. 9B is a rendering 900 of the console of FIG. 9A from a top rear perspective. The water supply tube 816 proceeds down through a U channel 922 in the reservoir 902. It then connects to the body of the shut off valve 914. A connection is then made to the console bulkhead fitting and first lumen 234 of the flexible supply tube.

A shelf 926 may be provided to support the reservoir. The console mouth rinse tube 904 can be seen emerging from the top of the reservoir 908. A clip 924 is provided to secure the console mouth rinse tube.

Massager Pick

Figure 10:
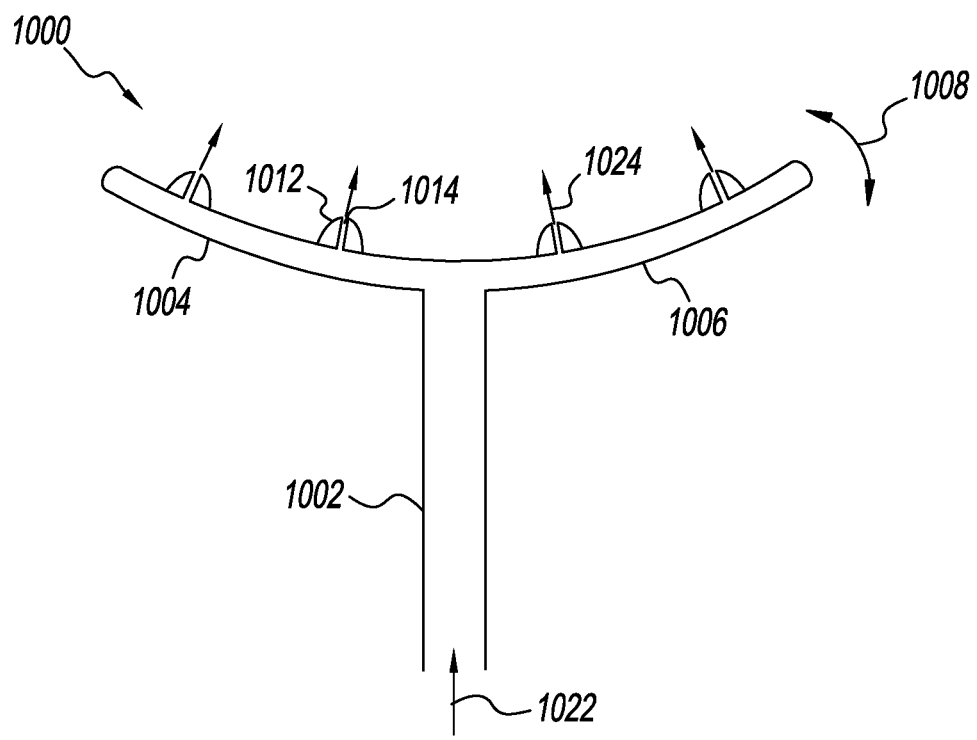
FIG. 10 is a drawing of a massager pick with left and right side branches and multiple exit orifices.

FIG. 10 is a drawing of a massager pick 1000. The massager pick may be used to massage a person's gums and/or clean said person's teeth. The massager pick comprises an inlet tube 1002 where fluid goes in 1022, a left side branch 1004 and a right side branch 1006. The left side branch and right side branch proceed horizontally from the distal end of the inlet tube. Said branches may be curved. Said branches may be flexible 1008. A plurality of exit orifices 1014 may be on said branches. Said exit orifices may all be on the same side of the branches. Thus when a massager pick is placed inside a user's mouth, the outlet water 1024 will impinge the same side of said person's teeth and gums.

Raised nubs 1012 may be provided on the left and right side branches. The orifices may proceed through said nubs. The nubs may be rubbed against a person's gums for a massaging effect. In alternative embodiment, only one branch may be provided in the massager pick.

Figure 11:
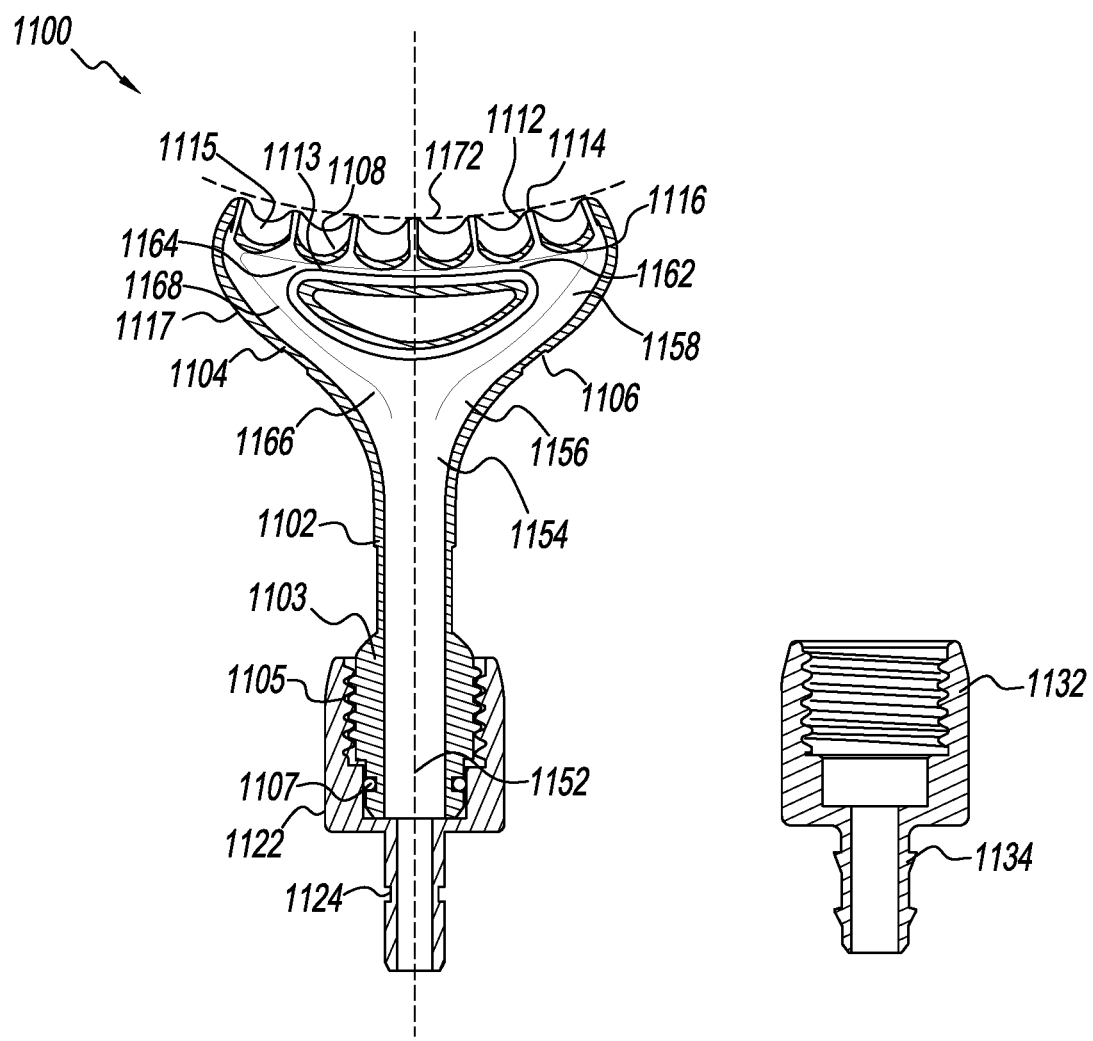
FIG. 11 is a longitudinal cross sectional rendering of an exemplary massager pick.

FIG. 11 is a longitudinal cross sectional rendering of an exemplary massager pick 1100. The massager pick comprises an inlet tube 1102, a hollow left side branch 1104, a hollow right side branch 1106 and a hollow bridge 1113. The inlet tube has an inlet 1152 and an outlet 1154. The left side branch has an inlet 1166 and an outlet 1168. The right side branch has an inlet 1156 and an outlet 1158. The bridge has a left end 1164, a right end 1162 and a top surface 1108. The outlet of the inlet tube is connected to the inlets of the left and right side branches. The outlets of the left and right side branches are connected to the left and right ends of the bridge. There is a plurality of exit orifices 1114 in the top surface of the bridge.

The bridge may have a longitudinal concave arcuate shape 1172. The inlet tube, left side branch, right side branch and bridge may be made from a rigid material 1117 such as plastic. The bridge may nonetheless be flexible enough so that it bends in or out when pressed against a surface with a smaller or larger radius of curvature than the radius of curvature of the concave arcuate shape. For example, the arcuate shape of the bridge may conform to the shape of a user's teeth or gums when the massager pick is pressed against them using the normal force a person could provide. It may then return to its original shape when removed from said person's mouth. Alternatively, the massager may be designed to conform to a person's mouth shape upon initial use and remain in said shape when removed from said person's mouth.

The upper wall of the bridge may form a plurality of upward directed converging nozzles 1116. The upward wall of the bridge may be covered with a layer of elastomer 1115 that is shaped into a plurality of upward directed nubs 1112. Each exit orifice passes through one of the upward directed nozzles and upward directed nubs.

The inlet tube 1102 may comprise an inlet fitting 1103. The inlet fitting may be adapted to reversibly connect to an adapter fitting 1122. A thread 1105 and O ring 1107 may be provided to connect the inlet fitting to the adapter fitting. The adapter fitting may comprise one of a number of alternative connection means, such as a quick disconnect 1124. FIG. 11 shows an alternative adapter fitting 1132 that comprises a tubing fitting 1134.

CONCLUSION

While the disclosure has been described with reference to one or more different exemplary embodiments, it will be understood by those skilled in the art that various changes may be made and equivalents may be substituted for elements thereof without departing from the scope of the disclosure. In addition, many modifications may be made to adapt to a particular situation without departing from the essential scope or teachings thereof. Therefore, it is intended that the disclosure not be limited to the particular embodiment disclosed as the best mode contemplated for carrying out this invention.

We claim:
1. An oral irrigator comprising:
 a) a water delivery system for connecting a source of high pressure water to an inlet of a pick;
 b) a mouth rinse delivery system for connecting a reservoir of mouth rinse to said inlet of said pick;
 c) a handle comprising:
  i) a blocking valve comprising:
   1) a blocking valve inlet;
   2) a blocking valve outlet;
   3) a body comprising an internal channel connecting said blocking valve inlet to said blocking valve outlet; and
   4) a spring loaded valve button wherein:
    a) said spring loaded valve button is biased to a normally open position; and
    b) said spring loaded valve button will close off said internal channel when urged closed; and
  ii) a hand pump comprising:
   1) a spring loaded piston at least in part defining a fluid chamber within the hand pump and movable to vary a volume of the fluid chamber, wherein said spring loaded piston is biased to a normally expanded configuration;
   2) a pump button attached to said spring loaded piston such that said spring loaded piston will be compressed when pressure is placed on said pump button;
   3) an inlet check valve fluidly connected to said fluid chamber and configured to allow fluid flow into said fluid chamber; and
   4) an outlet check valve fluidly connected to said fluid chamber and configured to allow fluid flow out of said fluid chamber;
 wherein
  said hand pump is mounted adjacent to said blocking valve such that said valve button will be urged closed when pressure is put on said pump button thus shutting off said source of high pressure water to said pick and allowing said mouth rinse to be pumped into said pick from said reservoir using said hand pump.
2. The oral irrigator of claim 1 which further comprises:
 a) a console comprising:
  i) said reservoir;
  ii) a mouth rinse tube; and
  iii) a water supply tube for connecting to said source of high pressure water; and
 b) a flexible supply tube comprising:
  i) a first lumen; and
  ii) a second lumen;
 wherein:
 c) said first lumen is part of said water delivery system and is adapted to convey said high pressure water from said water supply tube to said handle;
 d) said mouth rinse tube is part of said mouth rinse delivery system and is adapted to convey mouth rinse from said reservoir to said second lumen; and
 e) said second lumen is part of said mouth rinse delivery system and is adapted to convey mouth rinse from said mouth rinse tube to said handle.
3. The oral irrigator of claim 2 which further comprises said pick and wherein:
 a) said handle comprises a handle mount;
 b) said console comprises a console mount that mates with said handle mount;
 c) said reservoir comprises a top and a bottom;
 d) said pick is mounted on said handle; and
 e) said console mount is vertically positioned on said console such that an exit orifice of said pick will be above said top of said reservoir when said handle is mounted on said console such that mouth rinse will not be siphoned out of said reservoir.
4. The oral irrigator of claim 3 wherein said console mount is a stable cradle for said handle mount such that said handle will be held on said console by the force of gravity.
5. The oral irrigator of claim 3 wherein:
 a) said handle mount comprises a magnet and an overhang;
 b) said console mount comprises a magnet and a shelf; and
 c) said magnets will urge towards each other and said overhang will rest on said shelf when said handle is mounted on said console.
6. The oral irrigator of claim 3 wherein:
 a) said console comprises:
  i) a top;
  ii) a bottom; and
  iii) a console bulkhead fitting comprising a top and a bottom;
 b) said console bulkhead fitting is mounted on about said bottom of said console;
 c) said flexible supply tube is mounted into said bottom of said bulkhead fitting;
 d) said mouth rinse tube proceeds from said bottom of said reservoir over said top of said reservoir and connects to said top of said bulkhead fitting and hence to said second lumen of said flexible supply tube.
7. The oral irrigator of claim 1 wherein said spring loaded piston is an elastomeric bladder that will compress when said pump button is pressed and will expand when said pump button is released.
8. The oral irrigator of claim 1 which further comprises said pick and wherein:
 a) said handle comprises a pressure oscillator, said pressure oscillator comprising an inlet and an outlet;
 b) said outlet of said blocking valve is connected to said inlet of said pressure oscillator; and
 c) said outlet of said pressure oscillator is connected to said inlet of said pick.

9. The oral irrigator of claim 8 wherein said outlet check valve is connected to said outlet of said pressure oscillator.

10. The oral irrigator of claim 8 wherein said pressure oscillator comprises a turbine and wherein:
 a) said turbine comprises:
  i) an inlet with an inlet diameter;
  ii) an outlet with an outlet diameter;
  iii) a turbine housing comprising:
   1) a top;
   2) a bottom;
   3) a side wall, said side wall having a generally circular horizontal cross section comprising a center;
   4) a vertical axle connected to at least one of said top of said turbine housing or said bottom of said turbine housing; and
   5) said vertical axle is centered at about said center of said circular horizontal cross section; and
  iv) a turbine wheel comprising;
   1) a hub mounted on said vertical axle; and
   2) a plurality of vanes proceeding radially from said hub wherein:
    a) said vanes each comprise a length and a width;
    b) said vanes are about equally spaced apart on said hub; and
    c) each vane comprises a distal tip;
  b) said turbine inlet is adapted to introduce said high pressure water into said turbine housing in a tangential direction relative to said side wall; and
  c) said outlet of said turbine is in said top of said turbine housing.

11. The oral irrigator of claim 10 wherein there is a gap between said distal tips of said vanes and said side wall of said turbine housing.

12. The oral irrigator of claim 11 wherein said gap is at least 0.03 times said diameter of said circular cross section.

13. The oral irrigator of claim 10 wherein a closest distance from said turbine outlet and said turbine inlet is greater than the distance between the tips of two adjacent vanes.

14. The oral irrigator of claim 10 wherein:
 a) said pressure oscillator comprises a mouth rinse port;
 b) said mouth rinse port is downstream of said turbine outlet; and
 c) said outlet check valve is connected to said outlet of said pressure oscillator via said mouth rinse port.

15. The oral irrigator of claim 1 wherein said inlet of said blocking valve is collinear with said outlet of said blocking valve.

16. The oral irrigator of claim 15 wherein:
 a) said internal channel comprises a diameter;
 b) said inlet of said blocking valve comprise a diameter; and
 c) said diameter of said blocking channel is less than ½ of said diameter of said inlet of said blocking valve.

17. The oral irrigator of claim 15 which further comprises said pick and wherein:
 a) said pick comprises an exit orifice;
 b) said exit orifice of said pick comprises a diameter; and
 c) said diameter of said exit orifice is less than ½ of said diameter of said internal channel.

18. The oral irrigator of claim 1 wherein:
 a) said hand pump comprises a cylinder;
 b) said cylinder comprises a bottom with a recess in it; and
 c) said valve button of said blocking valve is located in said recess.

19. The oral irrigator of claim 1 wherein:
 a) said handle is dimensioned to fit in a person's hand; and
 b) said pump button is dimensioned and positioned to receive pressure from a thumb of the person's hand.

20. The oral irrigator of claim 1 wherein:
 a) said blocking valve is rigidly mounted within a housing of said handle; and
 b) said hand pump is flexibly mounted within said housing of said handle.

21. The oral irrigator of claim 1 which further comprises said pick and wherein said pick comprises a brush.

22. A massager pick for an oral irrigator comprising:
 a) a hollow left side branch comprising an inlet and an outlet;
 b) a hollow right side branch comprising an inlet and an outlet;
 c) an inlet tube comprising an inlet and an outlet; and
 d) a hollow bridge comprising a left end, a right end and a top surface wherein:
 e) said outlet of said inlet tube is connected to said inlet of said left side branch and said inlet of said right side branch;
 f) said left end of said bridge is connected to said outlet of said left side branch;
 g) said right end of said bridge is connected to said outlet of said right side branch;
 h) said top surface of said bridge is covered with an elastomeric layer and comprises a plurality of upward directed converging nozzles and a plurality of exit orifices, wherein said elastomeric layer is shaped to form a plurality of upward directed nubs and each of said exit orifices passes through one of said nozzles and one of said nubs.

23. The massager pick of claim 22 wherein:
 a) said bridge has a longitudinal concave arcuate shape with a radius of curvature;
 b) said bridge is flexible such that if it is pressed against a surface with a smaller or larger radius of curvature than said radius of curvature of said arcuate shape, said bridge will bend in or out.

* * * * *